(12) United States Patent
Patacca et al.

(10) Patent No.: US 7,476,697 B2
(45) Date of Patent: Jan. 13, 2009

(54) TOOTH COATING COMPOSITION

(76) Inventors: Thomas R. Patacca, 6326 Lastonia Rd., Independence, OH (US) 44131; Gregory G. Patacca, 6798 Meadowbrook Blvd., Independence, OH (US) 44131; Dean M. Frate, 3675 W. 135th St., Cleveland, OH (US) 44111

( * ) Notice: Subject to any disclaimer, the term of this patent is extended or adjusted under 35 U.S.C. 154(b) by 279 days.

(21) Appl. No.: 10/381,569

(22) PCT Filed: Sep. 10, 2001

(86) PCT No.: PCT/US01/42120

§ 371 (c)(1), (2), (4) Date: Nov. 24, 2003

(87) PCT Pub. No.: WO02/26196

PCT Pub. Date: Apr. 4, 2002

(65) Prior Publication Data
US 2004/0102554 A1     May 27, 2004

(51) Int. Cl.
*A61K 6/08* (2006.01)
(52) U.S. Cl. .................. 523/115; 523/116; 524/43; 524/111; 524/317; 524/379; 524/555
(58) Field of Classification Search .............. 523/115, 523/116; 524/43, 111, 317, 379, 555
See application file for complete search history.

(56) References Cited

U.S. PATENT DOCUMENTS

| 2,340,110 | A | 1/1944 | D'Alelio |
| 2,340,111 | A | 1/1944 | D'Alelio |
| 2,533,635 | A | 12/1950 | Seymour |
| 2,798,053 | A | 7/1957 | Brown |
| 3,940,351 | A | 2/1976 | Schlatzer, Jr. |
| 4,032,627 | A | 6/1977 | Suchan et al. |
| 4,062,817 | A | 12/1977 | Westerman |
| 4,496,322 | A | 1/1985 | Sandham et al. |
| 4,512,743 | A | 4/1985 | Santucci et al. |
| 4,648,845 | A | 3/1987 | Orlowski et al. |
| 4,883,534 | A | 11/1989 | Sandham et al. |
| 5,034,486 | A | 7/1991 | Tzai et al. |
| 5,034,487 | A | 7/1991 | Tazi et al. |
| 5,034,488 | A | 7/1991 | Tazi et al. |
| 5,160,737 | A | 11/1992 | Friedman et al. |
| 5,191,014 | A | 3/1993 | Roberts et al. |
| 5,330,746 | A | 7/1994 | Friedman et al. |
| 5,330,788 | A | 7/1994 | Roberts |
| 5,430,074 | A | 7/1995 | Barnes et al. |
| 5,438,076 | A | 8/1995 | Friedman et al. |
| 5,639,795 | A | 6/1997 | Friedman et al. |
| 5,648,399 | A | 7/1997 | Friedman et al. |
| 5,702,772 | A | 12/1997 | Skelly et al. |
| 5,916,674 | A | 6/1999 | Skelly et al. |
| 5,945,462 | A | 8/1999 | Salamon |
| 5,980,868 | A | 11/1999 | Homola et al. |
| 6,036,494 | A | 3/2000 | Cohen |
| 6,588,479 | B1 | 7/2003 | Kliskey |

FOREIGN PATENT DOCUMENTS

| EP | 0 404 558 A1 | 12/1990 |
| EP | 1 027 877 A1 | 8/2000 |
| EP | 1 112 750 A1 | 7/2001 |
| EP | 1 138 308 A2 | 10/2001 |

*Primary Examiner*—Bernard Lipman
(74) *Attorney, Agent, or Firm*—Roetzel & Andress; George W. Moxon, II

(57) ABSTRACT

A film forming composition for coating teeth which is a mixture of about 0.5% to about 30% by weight of a film forming polymer; about 10% to about 99.5% by weight of solvent; about 0.05% to about 40% by weight of a rheology modifier; about 0.01% to about 5% by weight of a dispersant or plasticizer, if necessary; and optionally up to about 30% by weight of an opacifier or colorant.

14 Claims, No Drawings

TOOTH COATING COMPOSITION

BACKGROUND OF THE INVENTION

The present invention is directed to a film forming coating for coating teeth. It is a temporary coating which will eventually wear off or may be easily removed when convenient or desired.

Temporary protective coatings or removable protective coatings are known. For example, U.S. Pat. No. 5,191,014, to Roberts et al., teaches a temporary protective aqueous coating composition which is applied to the hydrophobic paint work of newly finished motor vehicles, and yet is easily removable. The composition is a copolymer of (meth)acrylic acid, and a staple monomer, which creates a copolymer coating having a molecular weight of 10,000 to 200,000 that is soluble under alkaline conditions. U.S. Pat. No. 5,330,788, to Roberts, teaches a temporary coating to protect the surface of an article, which coating is weather resistant but soluble under alkaline conditions and which is a film-forming acrylic polymer. U.S. Pat. No. 5,916,674, to Skelly, et al., discloses an article having a removable protective film to protect the activated nature of an activated surface. The film-forming substance is water soluble, preferably a vinylpyrrolidone and vinyl acetate polymer. U.S. Pat. No. 5,945,462, to Salamon, discloses temporary protective coatings for precision surfaces such as glass, metals, ceramics, plastic and other materials of construction where the coating is a (meth)acrylate-capped organic prepolymer resin having at least one pendent hydrophilic group. This film-forming system is dependent on reactive curing of monomers and prepolymers.

There are patents which teach cosmetically improving and altering the appearance of teeth, such as U.S. Pat. No. 6,036,494, to Cohen, which teaches the use of a Bis-GMA (compound) (bisphenol diglycidylmethacrylate) or a glass ionomer. The coatings are reacted from monomers and/or prepolymers at the dental surface and can be pigmented. But once coated, it cannot be removed without using a dental pick or tool to remove the shell coating from the tooth. U.S. Pat. No. 5,980,868, to Homola, et al., discloses a dental delivery system for the protection of surfaces of teeth. The Homola composition provides a protective coating of fatty/waxy base which functions as a transfer agent or barrier stratum, but it does not appear to be a temporary removable coating. U.S. Pat. No. 4,512,743, to Santucci et al., teaches a polymerizable composition which can be applied to the surface of teeth, but it requires the etching of the tooth surface before applying the coating. U.S. Pat. Nos. 4,883,534, and 4,496,322, both to Sandham, et al., teach a varnish containing a dentally acceptable antimicrobial agent which can be painted on teeth to give a transparent, translucent or tooth colored film which is effectively invisible but provides sustained release of the antimicrobial agent. This is a film which is used to treat infection and can be removed by the application of the liquid varnish base. U.S. Pat. No. 5,430,074, to Barnes, et al., teaches a dental restoration kit which provides a gum-colored dental composite for restoring cavities and shorten the appearance of clinical crown on the facial surface of a tooth. The composition is a methacylate resin. The components are presented separately in a kit for combination and application to the tooth. The composition is reactive and is not considered a temporary removable composition. U.S. Pat. No. 4,032,627, to Suchan, et al., teaches a tooth whitening cosmetic composition that is applied temporarily and then removed with solvent. An alkaline solution is necessary for removal. U.S. Pat. No. 4,648,845, to Orlowski et al., teaches a method for indirect bonding of chemically or light curable resin-based restoratives such as acrylates and methacrylates to the base metal of dental cast restorations. The composition of Orlowski is not intended to be a temporary removable coating.

While the prior art coatings in general can be easily strippable, they are not suggested for use on teeth, and the coatings that are used for teeth which are removable require special tools or compositions to subsequently remove the coatings. The prior art coatings have been created from reactive monomers, prepolymers, and where necessary, highly reactive initiators like organic peroxides and light sensitive compounds. Any substantially reactive chemical system has the ability to affect the normal chemistry of living tissue and produce unsafe, unwanted, and sometimes toxic and detrimental changes. Likewise, the solvent systems described have included generally toxic compounds including reactive species. The prior art coatings have also been subject to removal or degradation by changes in acid/base balance, most notably toward basic conditions. Acidic and basic conditions are both found in day-to-day activities including eating and tooth brushing. When the conditions of film removal are found in common activities, the film is subject to premature and possibly unexpected and embarrassing removal.

SUMMARY OF THE INVENTION

The present invention is to a temporary or removable film forming composition for coating teeth which is a mixture of a natural or synthetic film forming polymer, a solvent, a rheology modifier, a dispersant or plasticizer, if necessary, and optionally an opacifier or colorant. It is applied to teeth preferably by brushing it on the tooth surface. The user can create temporary colors for the teeth or cover blemished or off color teeth. When the coating is no longer desired, it is readily stripped off. The film-forming system contained herein has several advantages over the cited prior art.

The film-forming system of the present invention comprises orally acceptable ingredients, which, individually, are described in the "Handbook of Pharmaceutical Excipients, $2^{nd}$ ed". The compounds of the present invention are acceptable and preferred for their demonstrated safety in pharmaceutical preparations. They also produce a film that shows no water solubility invariant of acid/base changes and which has a useful durability as a temporary and removable film. The present invention is a product that gives an aesthetically pleasing coating that is safe in its intended use, shows good performance over a planned duration, and is easily and safely removable when desired.

DETAILED DESCRIPTION OF THE INVENTION

The present invention is a film forming composition for coating teeth which is a mixture of a film forming polymer; a solvent; a rheology modifier; a dispersant or plasticizer, if necessary; and optionally an opacifier or colorant.

Film formers may be any of the natural polymers including commonly used gums, resins, exudates, animal rendering products and byproducts, such as gelatin and keratin, plant extracts, alginates, cellulose, galactomannans, bacterial products, such as Xanthan gum, and derivatives of these natural polymers, including methyl-, hydroxypropyl-, acetate phthalate, acetate, methoxy, hydroxypropoxy, acetyl, phthalyl, hydrolysates, and salts (Li, Na, K, Ca, Mg, Al, Zn, B. Fe, Cu, Ni), or combinations thereof or associated reaction byproducts. They may also be synthetic polymers, including homopolymers, copolymers, interpolymers, block polymers, or graft polymers, either crosslinked or substantially linear, derived from monomers known to film forming arts such as (meth)acrylic acid homo- and copolymers, including those to be found in U.S. Pat. Nos. 2,798,053; 3,940,351; 5,034,486; 5,034,487; 5,034,488; 4,062,817; 3,940,351; 2,340,110; 2,340,111; 2,533,635; the disclosures of which are incorporated herein by reference; and which are directed mainly at olefinically unsaturated moieties of various functionality and substitution. The film forming polymer is preferably an acrylic or methacrylic, i.e., (meth)acrylic acid polymer or copolymer, including acrylic acid, methyl acrylate, ethyl acrylate, methacrylic acid, methyl methacrylate, ethyl methacrylate, etc. A preferable acrylic polymer is available from Rohm Pharma GmbH as Eudragit RS 100 and it is the salt of a copolymer of ethyl acrylate, methyl methacrylate, and trimethyl ammonioethylmethacrylate. Other polymers that could be used include ethylcellulose, polyvinyl acetate, aminoalkyl methacrylate copolymer, chitin, chitosan, wax-type coatings, and the like. Another film forming polymer is Acrycoat acrylic and methacrylic polymers from Corel Pharma-Chem, Ahmedabad, India. What is important is that the polymer is appropriate for use in a mouth and forms a film, has sufficient strength, adheres, and can be subsequently removed. The film former is present in an amount of about 1% to about 30% by weight based upon the weight of the total mixture, although an amount of 5 to 20% by weight is preferred, with about 10% being further preferred.

Any solvent deemed suitable for the desired application/substrate may be used. This includes considerations of cost, color, ease of application, toxicology, environmental impact, regulatory status, effect on film formation and finished properties such as gloss, levelling, taste, flexibility, surface hardness, tensile strength, modulus, abrasion resistance, stain resistance, porosity, release/retention/absorbtion of target compounds, adhesion, cohesion, and ease of removal, e.g., methanol, ethanol, isopropanol, butanol, water, methylene glycol, ethylene glycol, propylene glycol, butylene glycol, neopentyl glycol, hexylene glycol, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, benzyl alcohol, and glycerin. The solvent is present in an amount of about 10% to about 99.5% by weight based upon the total weight of the mixture, although about 60% to about 90% by weight based upon the weight of the total mixture is preferred, with an amount of 80% by weight being further preferred.

The rheology modifier is selected to adjust the flow properties of the mixture so that it will remain on a vertical surface without running or creeping. The rheology modifier can be any of the known inorganic rheology modifiers such as clays, such as laponite, bentonite, and the like, and thickener grade silicas, which are well known for use in paints and coatings, commonly used gums, resins, exudates, animal rendering products and byproducts, such as gelatin or keratin, plant extracts, alginates, cellulose, galactomannans, bacterial products, such as Xanthan gum, and derivatives these compositions, including methyl-, hydroxypropyl-, acetate phthalate, acetate, methoxy, hydroxypropoxy, acetyl, phthalyl, hydrolysates, or salts (Li, Na, K, Ca, Mg, Al, Zn, B, Fe, Cu, Ni), or combinations thereof. They may also be synthetic polymeric rheology modifiers, including homopolymers, copolymers, interpolymers, block polymers, and graft polymers, either crosslinked or substantially linear, derived from monomers known to those skilled in rheology modification such as (meth)acrylic acid homo- and copolymers, including those to be found in U.S. Pat. Nos. 2,798,053; 3,940,351; 5,034,486; 5,034,487; 5,034,488; 4,062,817; 3,940,351; 2,340,110; 2,340,111; 2,533,635. A preferred rheology modifier is 2-hydroxypropyl cellulose. Other rheology modifiers could include crosslinked acrylic acid polymer and copolymers, such as Carbopol polymer from Noveon Inc. and Acrypol polymers from Corel Pharma-Chem, and the S-1700-L series of polymers from SNP, Inc. The rheology modifier is present in an amount of about 0.01% to about 40% by weight based upon the weight of the total mixture, although an amount of 1% by weight is preferred.

The dispersants may be chosen from many known in the arts concerned with particulate dispersion, particularly pigment dispersion, where compatible with the desired application and/or substrate. A dispersant or plasticizer may not be necessary if the polymer allows for the mixing and dispersion of the ingredients. Usually, this is not the case, but it will depend upon the polymer chosen. They may also be selected for reasons described in the choice of solvents above. e.g. sodium lauryl sulfate, polyoxyethylene alkyl ethers, polyoxyethylene castor oil derivatives, polyoxyethylene sorbitan fatty acid esters, polyethylene glycols (PEG), polypropylene glycols (PPG), polyethylene-polypropylene copolymers/block polymers (PEG/PPG), unsaturated polyoxyethylene ethers, silicone copolyols, perfluoroalkyl copolyols. The dispersant is present in an amount of about 0.01% to about 5% by weight based upon the weight of the total mixture, with an amount of 0.5% by weight being further preferred.

Plasticizers can be added specifically for the purpose of film property modification or may be added primarily for other functions including solvent, dispersant, or another film former. These additives are well known in the plastic and film forming arts, e.g., PEG, PPG, PEG/PPG, phthatlic esters, phosphoric esters, esters of adipic, azelaic, glutavic or sebacic acid, fatty acid esters or petaerithrol and their epoxides, citric esters, esters of acetic, propionic or butyric acid, esters of ethylbutyric or ethyl hexanoic acid, glycol esters, benzoic esters, trimellitic esters, sulfonic esters, sulfonamides, anilides, alcohols, ethers, ketones, and abietic derivatives. The dispersant is present in an amount of about 0.01% to about 5% by weight based upon the weight of the total mixture, although an amount of 0.5% by weight is preferred.

Colorants or opacifiers may include both soluble and insoluble compounds and their mixtures known to the arts concerned with coloring, e.g., titanium dioxide, iron oxides and their hydrates, carbon blacks, talc, clays, dyes, lakes, gold and various pigments. The colorant or opacifier is present in an amount of about 0% (i.e., none) to about 30% by weight based upon the weight of the total mixture, although an amount of about 1 to about 10% by weight is preferred. The colorant can be such as would match the surrounding teeth or could be in a non-tooth color, such as colors for athletic events, holidays, temporary gold teeth or glow-in-the-dark colors.

Additionally, compounds can be added specifically to promote other desireable qualities of the in-process product, finished product, or its resultant film. It is also possible to realize similar qualities from multi-functional ingredients added for other primary benefits. Such desireable qualities may include considerations listed in the choice of solvents above.

The composition of the present invention is primarily for use as a tooth coating, though it could be used as a protective barrier, a diffusion limiting, controlled release coating, a carrier for a drug substance, a low-concentration, long-duration bleaching or surface treating agent, an antimicrobial (chlorhexidines), or some similar application.

The composition is applied by spraying, brushing, or other convenient coating process. The process is not critical, although brushing is the most practical and is preferred.

Although the application devices is not critical, one convenient way of applying the composition would be a tube having a wicking device to deliver the coating to a tip which protrudes from the tube. The tip is then pressed against the tooth to deliver the coating. This type of device is similar to a "magic marker". Other devices include a container and brush similar to that for nail polish and the felt pads used for applying make-up.

The coating of the present invention is used as a cosmetic covering over undesirable appearing teeth. It can be applied to the surface of the tooth, but is not a permanent correction because it can be easily removed. It can be used to cover the surfaces of the teeth or to cover old and discolored fillings, or to cover the dark margins of crowns due to gum recession, or to coat crowns that no longer match so that the crown does not have to be replaced. It can also be used to cover a tooth that has a gray appearance due to root canal therapy or large amalgam fillings. The coating of the present invention does not alter the tooth in any way, except the color, and it is reversible. It is designed to be affordable because it does not require a licensed professional for bleaching, bonding, crowns, or veneers. Although not necessary, if desired, the surface of the tooth could be etched using a citric acid wash or a phosphoric acid (33% concentration) treatment (if done professionally by a dentist) to promote greater adhesion and a longer retention time.

The following example is illustrative of the present invention, and should not limit the scope of the invention.

EXAMPLE 1

| Ingredient | wt. % | Function |
| --- | --- | --- |
| Ethanol | 79.10 | Solvent/Preservative |
| Endragit RS 100 | 10.00 | Film Former/Rheology Modifier |
| Klucel HF Pharm | 00.60 | Rheology Modifier/Film Former |
| Tween 80 | 00.30 | Dispersant/Plasticizer |
| Titanium Dioxide | 10.00 | Opacifier/Colorant |
| Total: | 100.00 | |

Preparation:

1. (optional) Freeze grind Eudragit to a powdered form to facilitate its dissolution.
2. Dissolve Eudragit into ethanol.
3. Add Tween 20 to the Eudragit solution and disperse TiO2 in the same under high shear conditions (rotor-stator, colloid mill, ball mill, etc.). This may be done prior to step 1. where the shear necessary is detrimental to the film former(s).
4. Disperse Klucel into the Eudragit solution and mix at moderate shear (marine impeller, etc.) to fully dissolve and extend the Klucel.

Removal of the film coating may be easily and safely effected using a solution of 70% ethanol, or of similar composition as the original carrier solvent medium. This allows the removal of the film under controlled and mild conditions not likely to be found day-to-day in the oral cavity thus preventing its premature removal. The film in Example 1 has endured without significant change for four days, at which time it was easily removed in about one minute cleanly and completely with an 80% solution of ethanol in water.

Description of Selected Ingredients:

| Ingredient | Description | Source |
| --- | --- | --- |
| Eudragit RS 100 | A salt of a copolymer of ethylacrylate, methylmethacrylate and trimethylammonioethylmethacrylate (EA:MA:TMAEMA = 1:2:0.1); MW = 150,000 | Rohm Pharm GmbH |
| Klucel HF Pharm | 2-hydroxypropyl cellulose | Aqualon |
| Tween 80 | Polyoxyethylene sorbitan monoleate | ICI |

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated. It is intended that the invention be defined by the following claims.

What we claim is:

1. A film forming composition for coating teeth comprising the following:
    A) about 0.5% to about 30% by weight, based upon the weight of the composition, of a film forming polymer, wherein the film forming polymer is a salt of a copolymer of ethylacrylate, methylmethacrylate and trimethylammonioethylmethacrylate;
    B) about 10% to about 99.5% by weight, based upon the weight of the composition, of solvent;
    C) about 0.01% to about 40% by weight, based upon the weight of the composition, of a hydroxy propyl cellulose theology modifier; and
    D) optionally up to about 30% by weight, based upon the weight of the composition, of an opacifier or colorant.

2. The composition of claim 1 wherein the film forming polymer is selected from the group consisting of natural and synthetic polymers.

3. The composition of claim 1 wherein the film forming polymer is a (meth) acrylate copolymer.

4. The composition of claim 1 wherein the film forming polymer is present in an amount of about 1% to about 20.0% by weight.

5. The composition of claim 1 which further includes a dispersant or plasticizer.

6. The composition of claim 1 which further includes a dispersant or plasticizer in an amount of about 0.01% to about 15% by weight, based upon the weight of the composition.

7. The composition of claim 6 wherein the dispersant is polyoxyethylene sorbitan monoleate.

8. The composition of claim 6 wherein the dispersant or plasticizer is present in an amount of about 0.1% to about 5.0% by weight.

9. The composition of claim 1 wherein the solvent is ethanol.

10. The composition of claim 1 wherein the solvent is present in an amount of about 60.0% to about 80.0% by weight.

11. The composition of claim 1 wherein the rheology modifier is present in an amount of about 0.05% to about 40.0% by weight.

12. The composition of claim 1 wherein the opacifier is titanium dioxide.

13. The composition of claim 1 wherein the opacifier or colorant is present in an amount of about 0.01% to about 30% by weight.

14. A film forming composition for coating teeth comprising the following:

A) about 0.5 % to about 30% by weight, based upon the weight of the composition, of a film forming polymer;

B) about 10% to about 99.5% by weight, based upon the weight of the composition, of solvent C) about 0.01% to about 40% by weight, based upon the weight of the composition, of a hydroxy propyl cellulose rheology modifier, D) a dispersant or plasticizer in an amount of about 0.01% to about 15% by weight, based upon the weight of the composition, wherein the dispersant is polyoxyethylene sorbitan monoleate; and E) optionally up to about 30% by weight, based upon the weight of the composition, of an opacifier or colorant.

* * * * *